(12) United States Patent
Ikehara et al.

(10) Patent No.: US 8,258,675 B2
(45) Date of Patent: Sep. 4, 2012

(54) DETECTION SENSOR AND RESONATOR OF DETECTION SENSOR

(75) Inventors: Tsuyoshi Ikehara, Ibaraki (JP); Mitsuo Konno, Ibaraki (JP); Takashi Mihara, Tokyo (JP)

(73) Assignees: National Institute of Advanced Industrial Science and Technology, Tokyo (JP); Olympus Corporation, Tokyo (JP)

( * ) Notice: Subject to any disclaimer, the term of this patent is extended or adjusted under 35 U.S.C. 154(b) by 0 days.

(21) Appl. No.: 13/096,409

(22) Filed: Apr. 28, 2011

(65) Prior Publication Data

US 2011/0266919 A1    Nov. 3, 2011

Related U.S. Application Data

(63) Continuation of application No. PCT/JP2009/005587, filed on Oct. 23, 2009.

(30) Foreign Application Priority Data

Jul. 11, 2008   (JP) ................................ 2008-287018

(51) Int. Cl.
*H01L 41/08*    (2006.01)

(52) U.S. Cl. ...................................... 310/321; 310/331

(58) Field of Classification Search .................. 310/321, 310/322, 330–332
See application file for complete search history.

(56) References Cited

U.S. PATENT DOCUMENTS

| 5,162,691 | A  | * | 11/1992 | Mariani et al. ................ 310/321 |
| 5,856,722 | A  | * | 1/1999 | Haronian et al. ............. 310/321 |
| 6,223,601 | B1 | * | 5/2001 | Harada et al. .................... 73/649 |
| 7,369,115 | B2 | * | 5/2008 | Cruz-Hernandez et al. .. 345/156 |
| 8,169,124 | B2 | * | 5/2012 | Lee et al. ....................... 310/331 |
| 2006/0162455 | A1 | | 7/2006 | Kawakatsu |
| 2009/0225384 | A1 | * | 9/2009 | Eiji et al. .................... 359/199.1 |

FOREIGN PATENT DOCUMENTS

| JP | 2007-240252 A | 9/2007 |
| JP | 2008-241619 A | 10/2008 |
| WO | 2004-061427 A1 | 7/2004 |
| WO | 2008-069247 A1 | 6/2008 |

OTHER PUBLICATIONS

International Search Report for PCT/JP2009/005587; Jan. 19, 2010.

* cited by examiner

*Primary Examiner* — Mark Budd
(74) *Attorney, Agent, or Firm* — Pearne & Gordon LLP

(57) ABSTRACT

A detection sensor (10) includes: plural beam-like resonators (30A, 30B), a vibration characteristic of which changes according to adsorption or sticking of a substance having a mass and one end of each of which is fixed; a driving unit (40) that vibrates the resonators; and a detecting unit (40) that detects a change in the vibration in the resonators to detect the substance. The plural resonators have lengths different from one another. When the length of an arbitrary resonator is represented as L, a difference ΔL between the length L and the length of the other resonators is set to satisfy the following condition: 2(ΔL/L)>1/Q (Q represents a Q factor of the resonators). The driving unit vibrates the respective plural resonators at frequencies corresponding to resonant frequencies of the resonators.

9 Claims, 6 Drawing Sheets

DETECTION SENSOR AND RESONATOR OF DETECTION SENSOR

BACKGROUND OF THE INVENTION

Field of the Invention

The present invention relates to a detection sensor and a resonator of the detection sensor suitable for use in detecting the presence or absence of a substance having a mass, detecting the mass of the substance, or the like.

In the past, there has been a sensor for detecting the presence of gas or the like having explosion hazard and noxiousness or the quantitative concentration of the gas or the like. The sensor absorbs molecules of a specific type contained in the gas and detects the presence or absence of the absorption or an amount of the absorption to detect the presence or absence of the gas or the concentration of the gas. Such a sensor is set in a facility, an installation, an apparatus, or the like that handles the gas or the like and used for control of leakage of the gas and an amount of the gas.

In recent years, development of fuel cells is actively performed. Since hydrogen is used in the fuel cells, it is desirable to monitor whether leakage of the hydrogen occurs in a hydrogen station and vehicles, apparatuses, devices, and the like that use the fuel cells. The sensor can also be applied to such a use.

Besides the use, it is conceivable that the sensor for absorbing molecules of a specific type to detect the presence or absence of the absorption or an amount of the absorption is used for, for example, detecting organic molecules or odor molecules existing in the air to thereby perform, for example, analysis of freshness and components of foods, environmental control for providing and maintaining a comfortable atmosphere, and state detection for living organisms such as a human body.

A sensor element for detecting organic molecules, odor molecules, and the like existing in the air by observing a very small mass of the molecules, vibrates a resonator inside the sensor in surrounded gas containing these molecules and, when the molecules are adsorbed or stuck to the surface of the resonator, detects a mass change of the resonator as a change in a resonant frequency of the resonator.

As a most basic method of calculating an adsorbed mass from the change in the resonant frequency of the resonator, there is a QCM (Quartz Crystal Microbalance) method. In the QCM, a single crystal of quartz having piezoelectricity is cut in a plate shape to form a resonator and a voltage is applied to the resonator to cause shearing vibration called "thickness-shear mode vibration". It is known that a resonant frequency f of the resonator decreases by $\Delta f$ from an original resonant frequency $f_0$ when a substance having a mass $\Delta m$ is adsorbed to the surface of the resonator and an amount of $\Delta f$ is calculated as follows:

$$\Delta f/f_0 = -\Delta m/(m_0) \quad (1)$$

where, $m_0$ is the resonator mass.

On the other hand, a technique called MEMS (Micro Electro Mechanical Systems) for precisely processing a silicon thin film or the like with photolithography has been developed. The MEMS technique makes it possible to manufacture a resonator same as that in the QCM, which has been manufactured in a region of a mm (millimeter) scale, in a region of a μm (micrometer) scale. Since the size of the resonator is reduced, the resonator mass in Equation (1) substantially decreases and detection sensitivity for the adsorbed mass increases.

As the resonator for performing mass detection, besides, a resonator of a cantilever type that makes use of transverse vibration of a cantilever beam and a resonator of a disk type that makes use of in-plane vibration of a tabular resonator are mainly used (see, for example, Japanese Patent Laid-Open No. 2007-240252).

In both the resonators, changes in resonant frequencies of the resonators are calculated as follows:

$$\Delta f/f_0 = -\Delta m/(2m_0) \quad (2)$$

Although a coefficient is different from that in Equation (1), dependency of the resonator mass is the same.

The resonant frequency $f_0$ of the resonator of the cantilever type is as follows:

$$f_0 = \lambda_n^2/((4\sqrt{3})\pi) \times t/L^2 \times \sqrt{(E/\rho)} \quad (3)$$

where, t and L represent the thickness and the length of the resonator of the cantilever type respectively and E and $\rho$ represent the Young's modulus and the density of a substance constituting the resonator of the cantilever type respectively. When the resonator of the cantilever type is formed of silicon single crystal in parallel to the crystallographic <110> direction of the silicon single crystal, E=170 GPa and $\rho=2.33 \times 10^3$ kg/m³ should be used. $\lambda_n$ is a constant determined by the order n of vibration: $\lambda_1 = 1.875$, $\lambda_2 = 4.964$, $\lambda_3 = 7.855$, and the like. The frequency becomes higher in a higher-order mode.

The frequency response of the resonator of the cantilever type has width determined by a Q factor of vibration. The half-value width of the response is $f_H = f_0/Q$. When the resonator of the cantilever type is operated in the air under the atmospheric pressure for the purpose of odor sensing, the Q factor of the resonator of the cantilever type is generally determined by the viscosity of the air. The Q factor substantially depends on the dimensions of the resonator of the cantilever type. When the dimensions are thickness of 5 μm and length of 100 to 1000 μm, the Q factor is about 100 to 2000.

SUMMARY OF THE INVENTION

The mass sensor employing the resonator of the cantilever type only detects the adsorbed mass of molecules to the resonator and does not have a function of analyzing and identifying an adsorbed substance. The function of identifying an adsorbed substance is realized by the use of adsorption selectivity of a detection film applied to the surface of the resonator. Therefore, to perform more detailed analysis and identification of adsorbed molecules, plural kinds of detection films are respectively applied to plural resonators of the cantilever type and a difference in adsorption selectivity of each of the detection films is used. This method is widely used in the QCM. An adsorbed substance can be estimated from a difference in responsiveness of the plural detection films using a multivariate analysis or the like. In the QCM, analysis are performed typically using four to eight sensors.

In the resonator of the cantilever type, a number of microstructure can be simultaneously manufactured using a semiconductor manufacturing process. Therefore, plural resonators of the cantilever type can be easily fit in one small chip of a several millimeter square to realize a reduction in size of a sensor. The function of analyzing and identifying an adsorbed substance can be realized by applying plural kinds of detection films separately to the plural resonators of the cantilever type. In the QCM, detection units equivalent to the number of sensors need to be arranged. When the number of detection units arranged in a system is increased, the size of the system increases. There is an advantage that a system can be confined in an extremely small size even if the number of resonators of the cantilever type arranged is large.

However, a problem in that case is interference among the plural resonators of the cantilever type. There are two causes of the interference.

One cause is mechanical vibration interference. Since the resonators of the cantilever type are fixed on the same substrate in one chip, it is inevitable that, to a resonator of the cantilever type, vibration of other resonators of the cantilever type near the resonator is slightly transmitted. If there is an mechanical interaction among the plural resonators of the cantilever type having the same resonant frequency even a little, mutual resonance occurs, and a mechanical vibration characteristic changes, which result in the change of a resonant peak shape. For example, in the case of one resonator 1 of the cantilever type having the resonant frequency $f_0$ as shown in FIG. 5A, a vibration response has one peak as shown in FIG. 5B. On the other hand, if there is a mechanical interaction between two resonators 1A and 1B of the cantilever type having the same resonant frequency $f_0$ as shown in FIG. 6A, the two resonators 1A and 1B do not independently operate any more. As shown in FIG. 6B, the vibration mode is divided into a vibration mode in which the two resonators 1A and 1B operate in the same phase and a vibration mode in which the two resonators 1A and 1B operate in opposite phases. In general, in the mode of the same phase, a frequency is lower than the resonant frequency $f_0$ of the resonators 1A and 1B. In the mode of the opposite phases, a frequency is higher than the resonant frequency $f_0$ of the resonators 1A and 1B. For example, even if only one resonator 1A is caused to be operated, an operation mode becomes complicated by the mechanical influence of the other resonator 1B.

The other cause is electric interference. In general, to detect a resonant frequency change, the resonators 1A and 1B of the cantilever type are separately applied to an electrical feedback circuit to induce self-oscillation. However, when the oscillation circuits having the same frequency are present in the same housing, because of a crosstalk signal caused by a leak of an electromagnetic wave from a incomplete shield or grounding, it is likely that the two circuits affect each other, leading to an unstable operation.

A detection sensor of the present invention includes: plural beam-like resonators, a vibration characteristic of which changes according to adsorption or sticking of a substance having a mass and one end of each of the resonators is fixed; a driving unit that vibrates the resonators; and a detecting unit that detects a change in the vibration in the resonators to detect the substance. The plural resonators have lengths different from one another. When the length of an arbitrary resonator is represented as L, a difference $\Delta L$ between the length L and the length of the other resonators is set to satisfy the following condition:

$2(\Delta L/L) > 1/Q$ (Q represents a Q factor of the resonators)

The driving unit includes: a piezoelectric layer provided on one surface side of a substrate on which the plural resonators are provided; an electrode layer that applies a driving voltage to the piezoelectric layer; and an oscillation control unit that sequentially applies, as the driving voltage, an electric signal having a frequency corresponding to a resonant frequency of any one of the plural resonators to the electrode layer. Specifically, first, the oscillation control unit applies an electric signal having a frequency corresponding to a resonant frequency of any one first resonator among the plural resonators. Then, the resonator having the resonant frequency corresponding to the frequency of the applied electric signal vibrates. Thereafter, the oscillation control unit applies an electric signal having a frequency corresponding to a resonant frequency of a second resonator different from the first resonator. Then, the second resonator vibrates. In this way, the oscillation control unit sequentially changes a frequency of an electric signal to be applied. This makes it possible to sequentially vibrate the plural resonators.

The detecting unit detects a change in vibration response of a resonator having a resonant frequency corresponding to a frequency of an electric signal applied to the electrode layer by the oscillation control unit. A multiplexer or the like can be used for the switching of the plural resonators.

In another embodiment, the driving unit includes: plural piezoelectric layers provided near fixed ends of the respective resonators; electrode layers that apply driving voltages to the respective piezoelectric layers; and oscillation control units that apply, as the driving voltages, electric signals having frequencies set in advance to the respective electrode layers. The oscillation control units can also simultaneously vibrate the plural resonators independently by applying electric signals having frequencies corresponding to resonant frequencies of the resonators corresponding to the respective electrode layers to the electrode layers.

The detecting unit can detect the presence or absence of adsorption or sticking of a substance to a resonator. The detecting unit can also detect an amount of the substance adsorption to the resonator. If specific molecules or plural kinds of molecules having specific features or characteristics are caused to stick or adsorb to the resonator, the detection sensor can detect the specific molecules or the plural kinds of molecules having the specific features or characteristics.

When a detection film is applied to the surface of the resonator, the resonant frequency changes by a mass of the detection film. However, this can be approximately treated as a change in a material constant. For example, when a detection film having density $\rho_1$ is deposited by thickness $t_1$ on the entire one surface of a resonator having density $\rho$ and thickness t, Equation (3) can be applied by regarding average density as $(\rho_1 t_1 + \rho t)/(t_1 + t)$ and regarding thickness as $(t_1 + t)$. In general, an organic material has a smaller Young's modulus compared with silicon. The Young's modulus is typically E=3 MPa in a rubber material such as polybutadiene and is about E=3 GPa in a plastic material such as polystyrene having a relatively higher Young's modulus. Compared with E=170 GPa of silicon, the Young's modulus are smaller by two orders or more. Therefore, the influence of the detection film on the Young's modulus can be neglected. Since the Q factor has different influence depending on an resonator material, a change in the Q factor should be experimentally estimated. However, when the organic material is deposited relatively thinner than a resonator main body, usually, a large change is not induced.

According to the above examination, when the average density and the thickness change are applied to Equation (3), a resonant frequency of the resonator after the deposition of the detection film having the density $\rho_1$ and the thickness $t_1$ can be derived as follows:

$$f_1 = f_0 \times [1+(t_1/t)][1+(\rho_1/\rho) \times (t_1/t)]^{-1/2} \quad (4)$$

$$\approx f_0 \times [1-(1/2) \times (\rho_1/\rho)] \quad (5)$$

where the approximation that the thickness $t_1$ of the detection film is sufficiently smaller compared with the thickness of the resonator is used. As explained above, a resonant frequency of the resonator deposited with the detection film can be calculated by Equation (4).

On the surfaces of the resonators, detection films made of a material containing at least one of titanium dioxide, polyacrylic acid, polystyrene, polyacrylamine, polydimethylsiloxane, polyvinylchloride, polymethyl methacrylate, polybutadiene, and polystyrene copolymer are formed.

The present invention can be a set of detection sensor resonators including beam-like plural resonator main bodies, one end of each of the resonator main bodies is fixed, and detection films that are provided on the surfaces of the respective resonator main bodies and adsorb molecules. The plural resonator main bodies have lengths different from one another. When the length of an arbitrary resonator is represented as L, a difference ΔL between the length L and the length of the other resonators is set to satisfy the following condition:

$$2(\Delta L/L) > 1/Q \text{ (}Q\text{ represents a }Q\text{ factor of the resonators)}$$

The detection films are desirably formed containing at least one of titanium dioxide, polyacrylic acid, polystyrene, polyacrylamine, polydimethylsiloxane, polyvinylchloride, polymethyl methacrylate, polybutadiene, and polystyrene copolymer.

The plural resonator main bodies are desirably formed in a cavity formed on a substrate made of a silicon material.

DESCRIPTION OF SYMBOLS

10 . . . detection sensor, 20 . . . detection film, 30 . . . resonator (resonator main body), 30A, 30B . . . resonators, 30a . . . fixed end, 40 . . . driving/detecting unit (driving unit, detecting unit), 42 . . . frequency counter, 43 . . . piezoelectric layer, 44 . . . piezoelectric layer, 45 . . . oscillation control unit, 46 . . . vibration detection circuit, 47 . . . oscillation circuit, 48 . . . piezoresistive element, 49 . . . multiplexer, 50 . . . substrate, 51 . . . cavity Description Of Preferred Embodiments The present invention is explained in detail below on the basis of an embodiment shown in the accompanying drawings.

Figure 1:
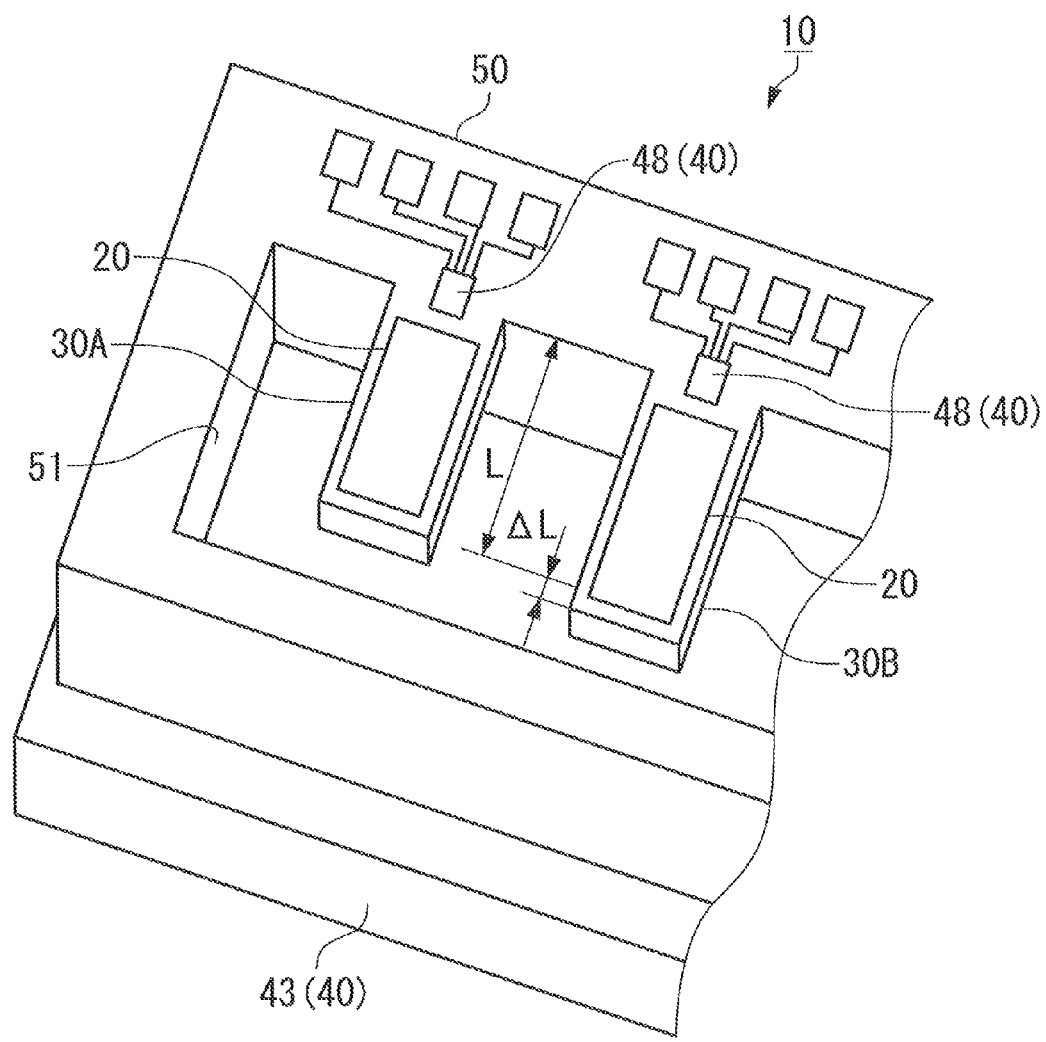
FIG. 1 is a perspective view showing, as an example of a detection sensor in an embodiment, a configuration in which a piezoelectric layer is provided on one surface of a substrate.

FIG. 1 is a diagram for explaining the configuration of a detection sensor 10 in this embodiment.

The detection sensor 10 shown in FIG. 1 adsorbs molecules of a specific type as a detection target (hereinafter simply referred to as molecules) to detect the presence (occurrence) or absence of gas, odor, or the like or the concentration of the gas, odor, or the like. The detection sensor 10 includes a set of resonators (resonator main bodies) 30A and 30B including detection films 20 that adsorb molecules and driving/detecting units 40 that detect adsorption of the molecules to the detection films 20.

The resonators 30A and 30B are cantilevers of a beam shape, one end of which is fixed. In the example shown in FIG. 1, only the two resonators 30A and 30B are shown. However, the number of resonators is not limited.

The resonators 30A and 30B are formed on the inside of a cavity 51, which is formed in the substrate 50 made of a silicon material, more specifically, polysilicon or single crystal silicon, by processing the substrate 50 using a MEMS technique such as a photolithography method. The resonators 30A and 30B have a rectangular shape in plan view and are made of the silicon material, particularly desirably single crystal silicon that constitutes the substrate 50.

As an example of the dimensions of the resonators 30A and 30B, it is desirable to set thickness to 2 to 5 μm, length to 30 to 1000 μm, and width to 10 to 300 μm.

Film-like detection films 20, to which molecules as a detection target are caused to stick or adsorb, are formed on the surfaces of the resonators 30A and 30B.

The detection films 20 can be formed of a film made of an inorganic material or an organic material. As the inorganic material forming the detection films 20, there is titanium dioxide ($TiO_2$) as a representative material. It is desirable to deposit titanium dioxide in a porous morphology and form the detection films 20 in order to improve adsorption efficiency. As the organic material forming the detection films 20, there are, for example, various polymers such as polyacrylic acid, polystyrene, polyacrylamine, polydimethylsiloxane, polyvinylchloride, polymethyl methacrylate, polybutadiene, and polystyrene copolymer. The detection films 20 can have molecule selectivity for adsorbing only a specific kind of molecules or plural kinds of molecules having specific features or characteristics. The selectivity depends on various factors such as a functional group forming a polymer and a state of cross-link.

Such detection films 20 are desirably formed to cover the upper surfaces of the resonators 30A and 30B.

In order to improve adhesion of a material forming the detection films 20 to the surfaces of the resonators 30A and 30B, it is desirable to form base bilayer films of Au (gold) and Cr (chromium) on the surfaces of the resonators 30A and 30B.

As shown in FIG. 1, as the driving/detecting units 40, it is possible to form a piezoelectric layer 43 on one surface side of the substrate 50 in order to vibrate the resonators 30A and 30B.

Figure 2:
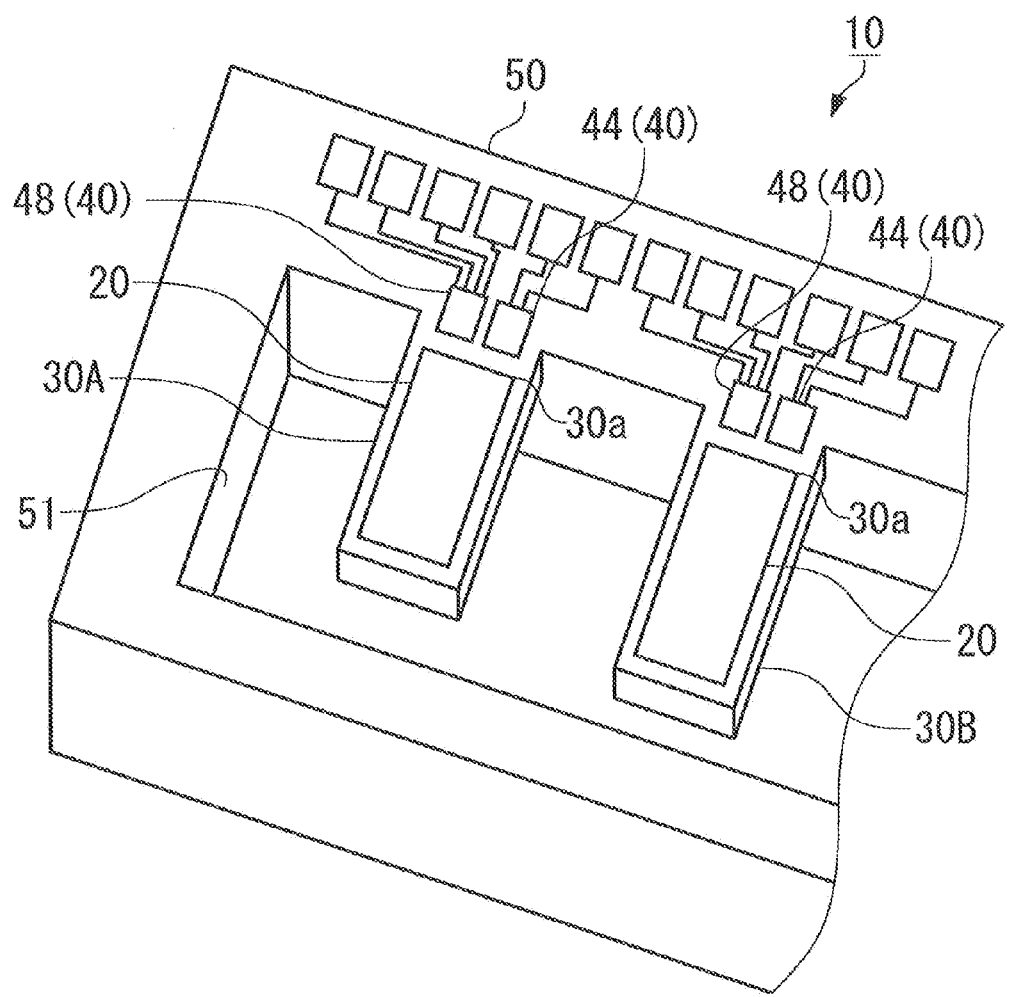
FIG. 2 is a perspective view showing, as another example of the detection sensor in the embodiment, a configuration in which piezoelectric layers are provided near fixed ends of resonators.

As shown in FIG. 2, as the driving/detecting units 40, piezoelectric layers 44 made of a piezoelectric material may be provided on the surfaces on a fixed ends 30a side of the resonators 30 in order to vibrate the resonators 30A and 30B.

As the piezoelectric material forming the piezoelectric layers 43 and 44, a ferroelectric material made of a material containing Pb, Zr, and Ti has been used. More specifically, the piezoelectric layers 43 and 44 can be made of a material obtained by crystallized Pb, Zr, and Ti (this material may be hereinafter referred to as PZT material). In the piezoelectric layer 43, the PZT material can be used either as a thin film or in bulk. The thickness of the piezoelectric layer 43 can be set to about 100 μm to 2 mm. On the other hand, in the piezoelectric layer 44, the PZT material needs to be formed as a thin film. The PZT material is formed at the thickness of, about 100 nm to 5 μm, for example. The thickness of the piezoelectric layer 44 can be realized by, for example, laminating plural layers of a thin film having thickness of 100 to several hundred nanometers per one layer.

As the piezoelectric material forming the piezoelectric layers 43 and 44, for example, Pb perovskite two-component/three-component ferroelectric ceramics can be used.

Besides the PZT material, ZnO (zinc oxide), AlN (aluminum nitride), non-lead perovskite structure ferroelectric ceramics, $BaTiO_3$ ceramics, $KNbO_3$—$NaNbO_3$ ferroelectric ceramics, $(Bi_{42}Na_{42})TiO_3$ ferroelectric ceramics, tungsten/bronze ferroelectric ceramics, $(Ba_{1-x}Sr_x)_2NaNb_5O_{15}$ [BSNN], $BaNa_{1-x}Bi_{x/3}Nb_5O_{15}$ [BNBN], bismuth layered structure ferroelectric and grain oriented ferroelectric ceramics, bismuth layered structure ferroelectric (BLSF), or the like may be used for the piezoelectric layers 43 and 44.

The electrode layer is formed on such piezoelectric layers 43 and 44.

Figure 3:
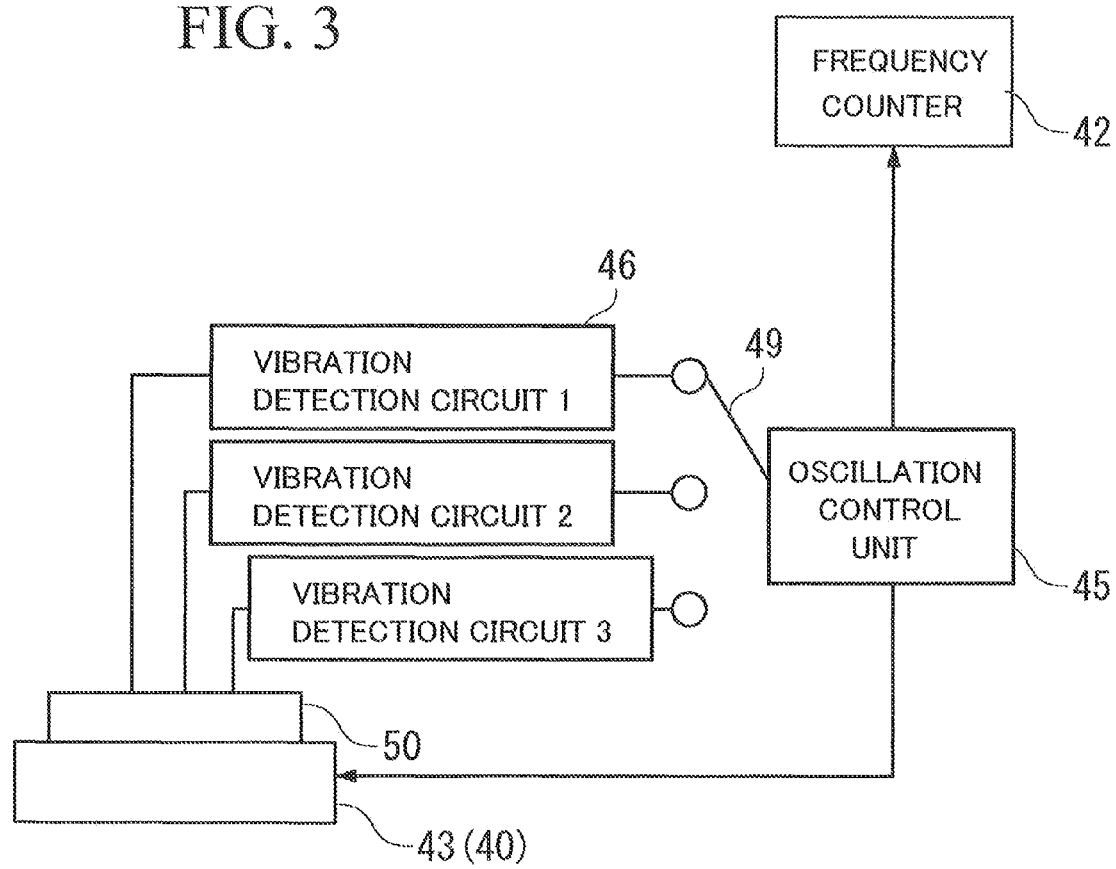
FIG. 3 is a diagram showing an example of a circuit configuration in the detection sensor shown in FIG. 1.

As shown in FIG. 3, such driving/detecting units 40 process, with an oscillation control unit 45 on the outside, a signal from a vibration detection circuit 46 and feeds back the signal to apply the processed signal to the electrode layer of the piezoelectric layer 43. Then, the piezoelectric layer 43 causes displacement, whereby self-oscillation of the vibrators 30A and 30B occurs. The driving/detecting unit 40 measures an oscillation frequency of the self-oscillation with a frequency counter 42.

When the piezoelectric layer 43 is provided along one surface of the substrate 50, as shown in FIG. 3, the oscillation control unit 45 applies a driving voltage at a frequency corresponding to a resonant frequency of any one of the plural resonators 30A and 30B and sequentially performs oscillation. In other words, first, the oscillation control unit 45 performs oscillation at a frequency corresponding to a resonant frequency of any one of the plural resonators 30A and 30B, for example, the resonator 30A. Subsequently, a signal input to the oscillation control unit 45 is switched by a multiplexer 49, whereby the oscillation control unit 45 performs oscillation at a frequency corresponding to a resonant frequency of the resonator different from the above, for example, the resonator 30B. In this way, a vibration detection signal given to the oscillation control unit 45 is sequentially changed by the multiplexer 49, whereby the oscillation control unit 45 sequentially vibrates the plural resonators 30A and 30B one by one.

Figure 4:
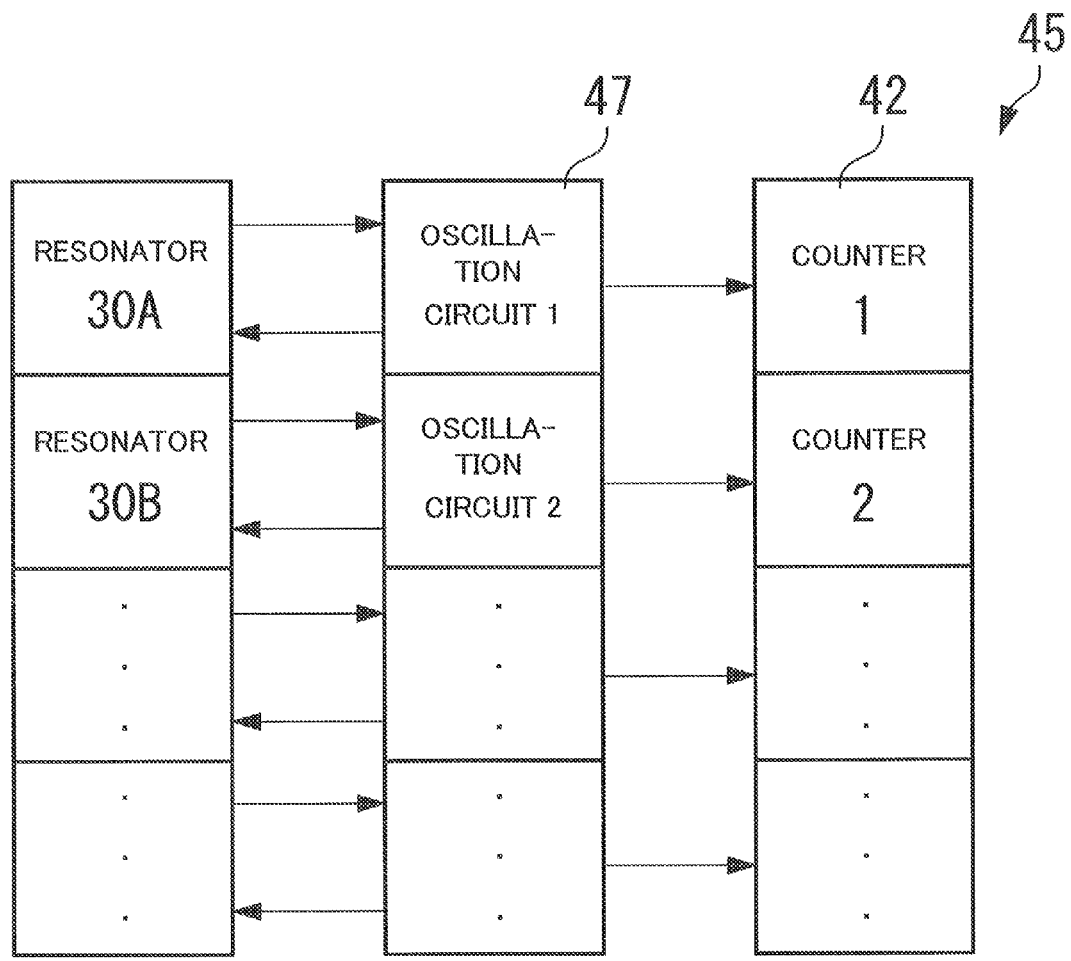
FIG. 4 is a diagram showing an example of a circuit configuration in the detection sensor shown in FIG. 2.
Figure 5A:
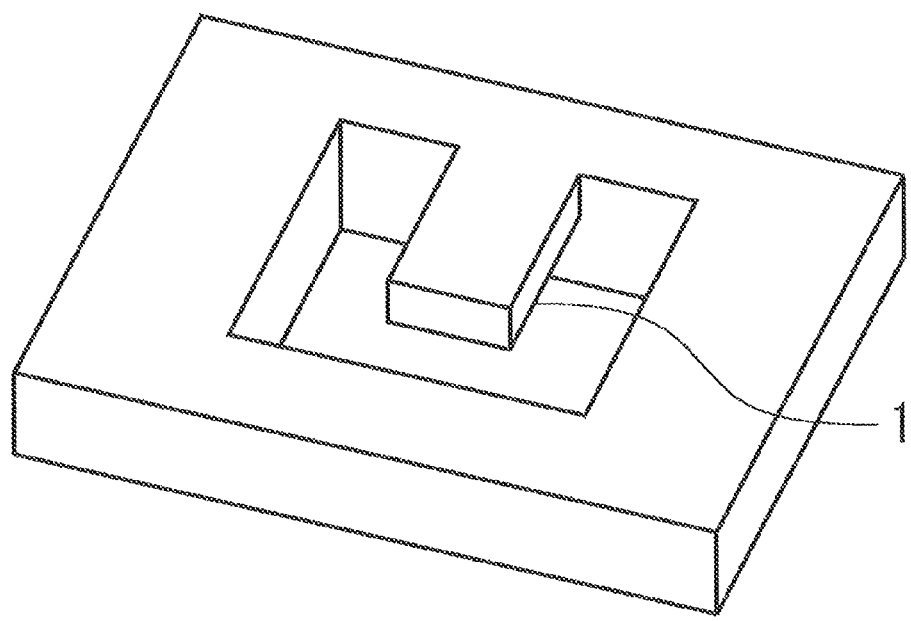
FIG. 5A is a perspective view showing a detection sensor in which one resonator is provided.
Figure 5B:
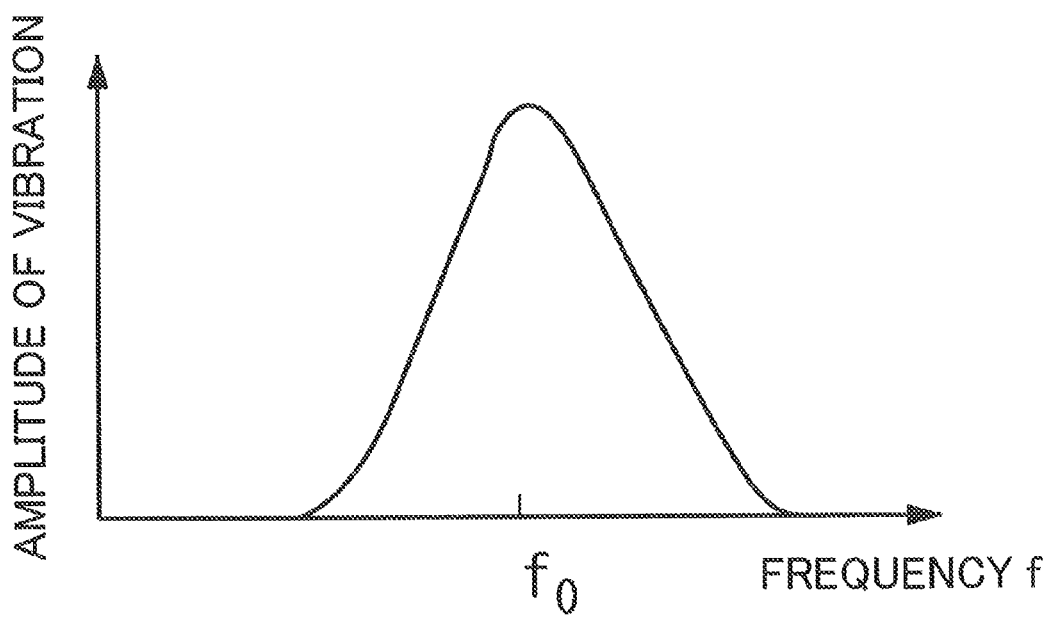
FIG. 5B is a diagram showing a relation between a frequency and amplitude response of vibration of the resonator in the detection sensor shown in FIG. 5A.
Figure 6A:
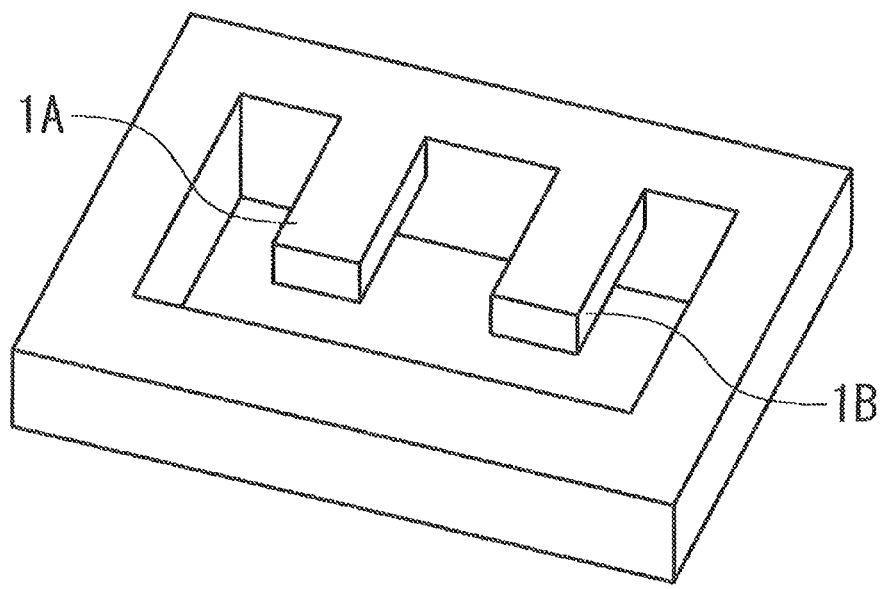
FIG. 6A is a perspective view showing a detection sensor in which two resonators having the same length are provided.
Figure 6B:
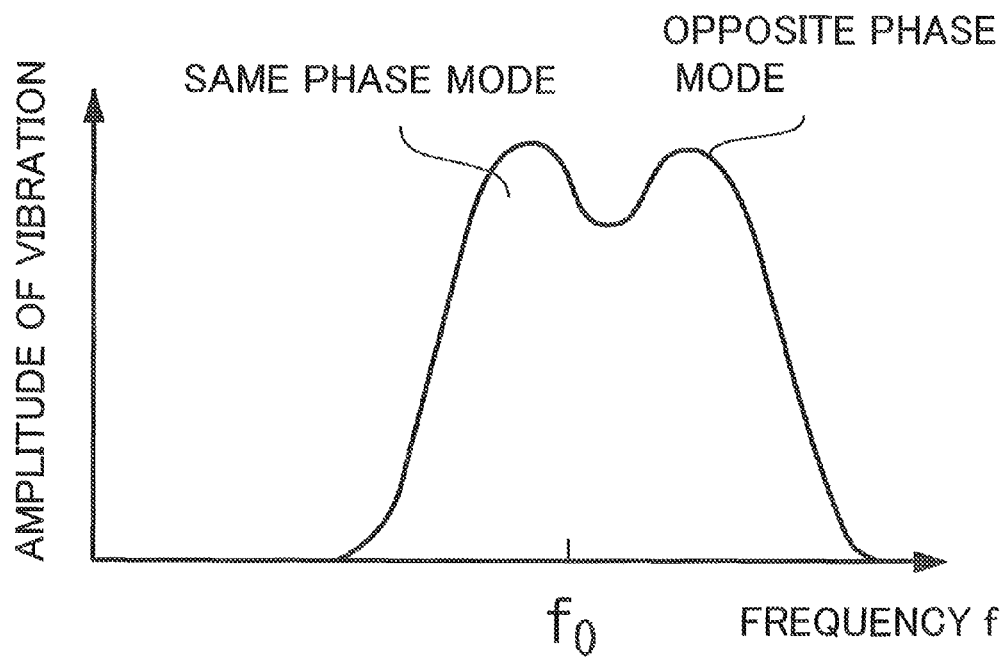
FIG. 6B is a diagram showing a relation between a frequency and amplitude response of vibration of the resonators in the detection sensor shown in FIG. 6A.

On the other hand, when the piezoelectric layers 44 are provided near fixed ends of the resonators 30A and 30B, as shown in FIG. 4, the oscillation control unit 45 includes an oscillation circuit 47 and the frequency counter 42 in each of the resonators 30A and 30B. The oscillation control unit 45 simultaneously drives the resonators 30A and 30B independently from one another. The oscillation circuit 47 is equivalent to a circuit obtained by combining the vibration detection circuit 46 and the oscillation control unit 45 shown in FIG. 3.

In order to select the order of vibration in vibrating the resonators 30A and 30B, it is desirable to provide, in the oscillation control unit 45, a band-pass filter that allows only a specific frequency to pass.

When a substance having a mass is adsorbed to the detection films 20 on the surfaces of the resonators 30A and 30B, the mass of the detection films 20 increases. When the mass of the detection films 20 increases according to adsorption of molecules, a resonant frequency of a system including the resonators 30A and 30B and the detection films 20 changes. The driving/detecting unit 40 detects the change in the resonant frequency of the resonators 30A and 30B according to the adsorption of the substance having a mass to the detection films 20. Therefore, as shown in FIGS. 1 and 2, piezoresistive elements 48 are provided near the fixed ends of the resonators 30A and 30B. The piezoresistive elements 48 are formed by impurity dopings on the surface of the substrate 50. Electric wires are connected to the piezoresistive elements 48 by patterning a metal thin film formed on the surface of the substrate 50. The resistance of the piezoresistive elements 48 changes according to a change in stress in the fixed-end sections of the resonators 30A and 30B at the time when the resonators 30A and 30B are deformed. The driving/detecting unit 40 detects the change in the resonant frequency of the resonators 30A and 30B by measuring the change in the resistance. This makes it possible to measure the presence or absence of adsorption of molecules to the detection films 20 or a adsorbed amount of the molecules.

When the configuration shown in FIG. 1 is adopted, as shown in FIG. 3, in the oscillation control unit 45, the multiplexer 49 is provided in a driving circuit. A signal input to the oscillation control unit 45 is switched by a multiplexer 49, whereby the driving/detecting unit 40 detects a resistance change in the piezoresistive element 48 provided in one resonator corresponding to a frequency of a driving voltage applied to the piezoelectric layer 43 by the oscillation control unit 45 among the resonators 30A and 30B.

In order to cause the resonators 30A and 30B to perform self-oscillation, the oscillation control unit 45 desirably amplifies a vibration output extracted from the piezoresistive elements 48 of the resonators 30A and 30B and gives the vibration output to the piezoelectric layers 43 and 44 with a necessary phase shift given to the vibration output to form a feedback circuit. With such a circuit, self-oscillation at the resonant frequency of the resonators 30A and 30B occurs.

In the configuration explained above, in the present invention, the lengths of the resonators 30A and 30B are set to be different from one another.

Each of the plural resonators 30A and 30B is formed such that a difference $\Delta L$ between the length L of the resonator and the length of the other resonators satisfies the following relation.

In general, according to Equation (3), when a resonant frequency of a resonator having the length L is represented as $f_0$, a difference $\Delta f_0$ between the resonant frequency of the resonator having the length L and a resonant frequency of a resonator having length $L+\Delta L$ is as follows:

$$\Delta f_0 \approx f_0 \times 2\Delta L/L$$

where $\Delta L$ and L are approximated as $\Delta L \ll L$. If the difference $\Delta f_0$ is sufficiently larger than half-value width $f_H = f_0/Q$ of a vibration mode, resonant peaks do not overlap. Q is a Q factor of a resonator. Since this condition becomes $\Delta f_0 > f_H$, as a result, the difference $\Delta L$ between the lengths only has to be given to satisfy the following condition:

$$2(\Delta L/L) > 1/Q \qquad (6)$$

When the detection sensor includes plural resonators, if the difference $\Delta L$ between the length of an arbitrary resonator and the length of the other resonators satisfies Expression (6), it is possible to prevent an interference effect caused by transmission of vibration among the resonators.

As explained above, the plural resonators 30A and 30B having the different lengths operate at different frequencies. Therefore, even if the plural resonators 30A and 30B are caused to simultaneously operate, the resonators 30A and 30B stably operate without interfering with one another. Even if each of the resonators 30A and 30B is caused to independently operate, since the frequency of the resonator is different from the frequency of the other resonators, mechanical interaction is small and the influence among the resonators 30A and 30B can be reduced. Therefore, each of the resonators 30A and 30B has an independent resonant peak and stable oscillation can be secured. As a result, even very small resonant frequency shifts of the respective resonators 30A and 30B can be measured. As a result, molecule detection sensitivity is improved.

In the configuration shown in FIG. 2, even when the plural resonators 30A and 30B are caused to simultaneously oscillate, since the frequencies are different, electric interference less easily occurs and stable oscillation can be performed. This makes it possible to detect molecules simultaneously in the plural resonators 30A and 30B. Therefore, it is possible to capture frequency changes in the plural resonators 30A and 30B in a short time. If measurement of all the resonators 30A and 30B is performed within a fixed time, it is possible to secure a long measurement time for one resonator. As a result, frequency measurement accuracy is improved and molecule detection sensitivity is improved.

Therefore, it is possible to perform measurement of the plural resonators 30A and 30B in time same as time for measurement of a single resonator. With the detection sensor including such plural resonators 30A and 30B, the function of analyzing and identifying a substance adsorbed by the detection films 20 can be improved by applying plural kinds of detection films 20 separately to the detection films 20 of the plural resonators 30A and 30B. On the other hand, it is unnecessary to strictly perform mechanical insulation and electric shield of circuits in the substrate 50 included in the detection sensor 10. Therefore, it is possible to reduce the size of an apparatus.

EXAMPLE 1

An operation test was performed concerning the plural resonators of the cantilever type having the different lengths as explained above.

The resonators were manufactured from an SOI (Silicon on Insulator) substrate including an SOI layer having thickness of 5 μm. The SOI layer was etched into a shape of the resonators by the photolithography technique to manufacture a fine resonator structure. A layer of the substrate under the resonators was etched from the rear surface to form a cavity and enable the resonators to freely vibrate in the air.

In order to detect deformation of the resonators due to vibration, piezoresistive elements were arranged at the fixed-end of the resonators. The piezoresistive elements were manufactured by impurity dopings on the surface of the substrate. Electric wires were connected to the piezoresistive elements by patterning a metal thin film formed on the surface of the substrate. The piezoresistive elements sense stress at the fixed-end due to the deformation of the resonators and the resistance of the piezoresistive elements changes. Therefore, the vibration of the resonators was detected by measuring the resistance.

A base film of an Au thin film was formed in order to apply detection films on the resonators.

In order to vibrate the resonators, one PZT plate was bonded to the lower surface of the substrate as a piezoelectric layer. In order to cause the resonators to perform self-oscillation, vibration outputs extracted from the piezoresistive elements of the resonators were amplified and given to the piezoelectric layer with a necessary phase shift given to the vibration outputs to form a feedback circuit. In such a circuit, self-oscillation at resonant frequencies of the resonators occurred. The frequency of the self-oscillation was measured by a frequency counter. In order to select the order of vibration, a band-pass filter that allows only a specific frequency to pass was provided in an oscillation control unit.

In this configuration example, since the piezoelectric layer was provided on the outside of the resonators, a vibration plate was shared by all the resonators. Therefore, the resonators having different resonant frequencies were not able to be oscillated simultaneously. Therefore, measurement was sequentially performed using a multiplexer.

A resonator having length of 500 μm and thickness of 5 μm is examined. From Q factor measurement of the resonators manufactured as explained above, it was actually measured that a Q factor of vibration was 210 in vibration in a primary mode, 590 in a secondary mode, and 950 in a tertiary mode. Therefore, the condition of Expression (6) was $\Delta L>1.2$ μm in the primary mode, $\Delta L>0.4$ μm in the secondary mode, and $\Delta L>0.3$ μm in the tertiary mode. The length change $\Delta L$ was set to 3 μm taking into account a manufacturing error and resonant frequencies in the primary to tertiary oscillation modes. Resonant frequencies were calculated in nine kinds of resonators using Equation (3) and results shown in the following table were obtained. The Young's modulus E and the density $\rho$ of the resonators were E=170 GPa and $\rho=2.33\times10^3$ kg/m$^3$.

TABLE 1

| Thickness | Length | Resonant frequency (kHz) | | |
|---|---|---|---|---|
| (μm) | (μm) | Primary | Secondary | Tertiary |
| 5.0 | 512 | 26.32 | 164.93 | 461.85 |
| 5.0 | 509 | 26.63 | 166.88 | 467.31 |
| 5.0 | 506 | 26.94 | 168.86 | 472.87 |
| 5.0 | 503 | 27.27 | 170.88 | 478.52 |
| 5.0 | 500 | 27.59 | 172.94 | 484.28 |
| 5.0 | 497 | 27.93 | 175.03 | 490.15 |
| 5.0 | 494 | 28.27 | 177.17 | 496.12 |
| 5.0 | 491 | 28.61 | 179.34 | 502.20 |
| 5.0 | 488 | 28.97 | 181.55 | 508.39 |

It is seen from the calculation results that, in the resonators having the length difference of 3 μm, the resonant frequencies shift by about 0.3 kHz in the primary mode, about 2 kHz in the secondary mode, and about 6 kHz in the tertiary mode. On the other hand, from the Q factor measurement of the actually-manufactured resonators (having length of 500 μm), the half-value width $f_H$ in frequency response of vibration was 0.13 kHz in the primary mode, 0.30 kHz in the secondary mode, and 0.53 kHz in the tertiary mode. Therefore, a difference among the resonant frequencies of the resonators having the different lengths is always sufficiently larger than the half-value width of the vibration mode and vibration peaks can be separated as designed. It is possible to cause the nine resonators manufactured in such a design to operate without mechanically and electrically interfering with one another even if the resonators are placed in the same chip.

EXAMPLE 2

Example 2 corresponds to the configuration shown in FIG. 2. Piezoelectric layers arranged on respective resonators were used. Otherwise, Example 2 is the same as Example 1.

The resonators were able to be caused to simultaneously oscillate at frequencies different from one another. Therefore, it is possible to simultaneously perform measurement of frequencies and perform parallel detection at high speed.

EXAMPLE 3

Example 3 is an example in which different kinds of detection films are applied to two resonators A and B. Both the thicknesses of the resonators A and B were 5 μm. The resonator A had a length of L=500 μm and the resonator B had a length of 500 μm+ΔL. Polybutadiene (PBD) (density $\rho_1$=1.01 g/cm$^3$) was deposited to the resonator A as a detection film at thickness of $t_1$=500 nm. Polystyrene (PS) (density $\rho_2$=1.05 g/cm$^3$) was deposited to the resonator B at thickness of $t_2$=500 nm. The Q factor of the resonators A and B was 210 in the primary mode.

For comparison, a resonator C, the length of which was set to 500 μm same as that of the resonator A and a detection film of which was made of polystyrene same as that of the resonator B, was manufactured.

Conditions under which primary vibration peaks do not overlap is calculated as follows:

$$2(\Delta L/L) > 1/Q + (t_2/t) \times [1-(\rho_2/\rho)] - (t_1/t) \times [1-(\rho_1/\rho)] \quad (7)$$

When the parameters are applied to the expression, ΔL>0.98 μm. When resonant frequencies were calculated by Equation (4) with ΔL set to 2 μm taking into account a manufacturing error, results shown in Table 2 were obtained.

TABLE 2

|  | Thickness (μm) | Length (μm) | Density (g/cm$^3$) | Detection film material | Film thickness (μm) | Film density (g/cm$^3$) | Average density (g/cm$^3$) | Primary resonant frequency (kHz) |
|---|---|---|---|---|---|---|---|---|
| Resonator A | 5.0 | 500 | 2.33 | PBD | 0.5 | 1.01 | 2.210 | 31.17 |
| Resonator B | 5.0 | 502 | 2.33 | PS | 0.5 | 1.05 | 2.214 | 30.89 |
| Resonator C | 5.0 | 500 | 2.33 | PS | 0.5 | 1.05 | 2.214 | 31.14 |

It is seen from Table 2 that a difference of 0.28 kHz occurred between resonant frequencies of the two resonators A and B, to the lengths of which the difference of 2 μm was given. The value 0.28 kHz is larger than the half-value width $f_H$=0.13 kHz in the frequency response of the vibration in the primary mode and indicates that the design standard of Expression (7) is appropriate.

On the other hand, in the case of the resonator C, the length of which is the same as that of the resonator A, a difference in a resonant frequency from that of the resonator A having the different type of the detection film is 0.03 kHz, which is smaller than the half-value width of the frequency response. The resonator A and the resonator C are considered to interfere with each other.

As explained above, even when the detection films having the different lengths are applied, it is possible to integrate the resonators such that resonant peaks do not interfere by giving a difference to the lengths of the resonators.

In the embodiment, the piezoelectric layers 43 and 44 can be provided in positions, ranges, and the like other than those explained above. For example, piezoelectric layers may be provided on the resonators 30A and 30B. Besides, as a driving system for the resonators 30A and 30B and a detection system for a vibration change, systems other than those explained above can be adopted.

Besides, the components explained in the embodiment can be sorted out or can be changed to other components as appropriate without departing from the spirit of the present invention.

The invention claimed is:

1. A detection sensor comprising:
   plural beam-like resonators, a vibration characteristic of which changes according to adsorption or sticking of a substance having a mass and one end of each of the resonators is fixed;
   a driving unit that vibrates the resonators; and
   a detecting unit that detects a change in the vibration in the resonators to detect the substance, wherein
   the plural resonators have lengths different from one another and, when a length of an arbitrary resonator is represented as L, a difference ΔL between the length L and length of the other resonators is set to satisfy the following condition:

$2(\Delta L/L) > 1/Q$ (Q represents a Q factor of the resonators), and the driving unit vibrates the respective plural resonators at frequencies corresponding to resonant frequencies of the resonators.

2. The detection sensor according to claim 1, wherein the driving unit includes:
   a piezoelectric layer provided on one surface side of a substrate on which the plural resonators are provided;
   an electrode layer that applies a driving voltage to the piezoelectric layer; and
   an oscillation control unit that sequentially applies, as the driving voltage, an electric signal having a frequency corresponding to a resonant frequency of any one of the plural resonators to the electrode layer, and
   the detecting unit detects a change in vibration of the resonator having the resonant frequency corresponding to the frequency of the electric signal applied to the electrode layer by the oscillation control unit.

3. The detection sensor according to claim 1, wherein the driving unit includes:
   piezoelectric layers provided near fixed ends of the respective resonators;
   electrode layers that apply driving voltages to the respective piezoelectric layers; and
   oscillation control units that are provided in the respective electrode layers and apply, as the driving voltages, electric signals to the piezoelectric layers, wherein
   the oscillation control units simultaneously vibrate the plural resonators independently by applying electric signals having frequencies corresponding to resonant frequencies of the resonators corresponding to the respective electrode layers to the electrode layers.

4. The detection sensor according to claim 1, wherein the detecting unit detects an amount of the substance adsorbed to the resonators.

5. The detection sensor according to claim 1, wherein the substance is specific molecules or plural kinds of molecules having specific features or characteristics.

6. The detection sensor according to claim 1, wherein detection films made of a material containing at least one of titanium dioxide, polyacrylic acid, polystyrene, polyacrylamine, polydimethylsiloxane, polyvinylchloride, polymethyl methacrylate, polybutadiene, and polystyrene copolymer are formed on surfaces of the resonators.

7. A resonator of a detection sensor comprising:
beam-like plural resonator main bodies, one end of each of the resonator main bodies is fixed; and
detection films that are provided on surfaces of the respective resonator main bodies and adsorb molecules, wherein
the plural resonator main bodies have lengths different from one another and, when the length of an arbitrary resonator is represented as L, a difference $\Delta L$ between the length L and length of the other resonators is set to satisfy the following condition:

$2(\Delta L/L) > 1/Q$ ($Q$ represents a $Q$ factor of the resonators).

8. The resonator of a detection sensor according to claim 7, wherein the detection films are formed containing at least one of titanium dioxide, polyacrylic acid, polystyrene, polyacrylamine, polydimethylsiloxane, polyvinylchloride, polymethyl methacrylate, polybutadiene, and polystyrene copolymer.

9. The resonator of a detection sensor according to claim 7, wherein the plural resonator main bodies are formed in a cavity formed on a substrate made of a silicon material.

* * * * *